United States Patent
Yin

(10) Patent No.: US 8,613,941 B1
(45) Date of Patent: Dec. 24, 2013

(54) SYNERGISTIC ANTIMICROBIAL COMPOSITION

(71) Applicant: Dow Global Technologies LLC, Midland, MI (US)

(72) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/025,862

(22) Filed: Sep. 13, 2013

Related U.S. Application Data

(62) Division of application No. 13/382,407, filed on Jan. 5, 2012, now Pat. No. 8,557,266.

(51) Int. Cl.
*A01N 57/18* (2006.01)
*A01N 47/08* (2006.01)
*A01N 33/18* (2006.01)

(52) U.S. Cl.
USPC .............. 424/405; 514/77; 514/129; 514/579

(58) Field of Classification Search
None
See application file for complete search history.

(56) References Cited

U.S. PATENT DOCUMENTS

| | | | |
|---|---|---|---|
| 3,981,998 A | 9/1976 | Waldstein | |
| 4,978,512 A | 12/1990 | Dillon | |
| 5,094,890 A | 3/1992 | Smith et al. | |
| 5,347,004 A | 9/1994 | Rivers et al. | |
| 5,385,896 A | 1/1995 | Bryan et al. | |
| 2008/0004189 A1 | 1/2008 | Smith et al. | |

FOREIGN PATENT DOCUMENTS

JP    11222408    8/1999

OTHER PUBLICATIONS

EPA RED Facts., Tris(hydoxymethyl)nitromethane, 1993, http://www.epa.gov/oppsrrd1/REDs/factsheets/3149fact.pdf.

*Primary Examiner* — Juliet C Switzer
*Assistant Examiner* — Kauser M Akhoon
(74) *Attorney, Agent, or Firm* — Kenneth Crimaldi

(57) ABSTRACT

A synergistic antimicrobial composition comprising:
(a) a hydroxymethyl-substituted phosphorus compound selected from the group consisting of tetrakis(hydroxymethyl)phosphonium salts and tris(hydroxymethyl)phosphine; and
(b) tris(hydroxymethyl)nitromethane.

3 Claims, No Drawings

SYNERGISTIC ANTIMICROBIAL COMPOSITION

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. For example, U.S. Pat. No. 5,385,896 discloses combinations of phosphonium salts and aldehydes, but this reference does not suggest any of the combinations claimed herein. Moreover, there is a need for additional combinations of antimicrobial compounds having enhanced activity to provide effective control of microorganisms. The problem addressed by this invention is to provide such combinations of antimicrobial compounds.

STATEMENT OF THE INVENTION

The present invention is directed to a synergistic antimicrobial composition comprising: (a) a hydroxymethyl-substituted phosphorus compound selected from the group consisting of tetrakis(hydroxymethyl)phosphonium salts and tris(hydroxymethyl)phosphine; and (b) tris(hydroxymethyl)nitromethane (Tris Nitro); wherein a weight ratio of the hydroxymethyl-substituted phosphorus compound to tris(hydroxymethyl)nitromethane is from 8:1 to 1:12.

DETAILED DESCRIPTION OF THE INVENTION

As used herein, the following terms have the designated definitions, unless the context clearly indicates otherwise. The term "antimicrobial compound" refers to a compound capable of inhibiting the growth or propagation of microorganisms, and/or killing microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. The hydroxymethyl-substituted phosphorus compound is selected from the group consisting of tetrakis(hydroxymethyl)phosphonium salts (e.g., tetrakis(hydroxymethyl)phosphonium sulfate (THPS) and tetrakis(hydroxymethyl)phosphonium chloride) and tris(hydroxymethyl)phosphine. More than one hydroxymethyl-substituted phosphorus compound may be present, in which case the biocide ratio is calculated from the total content of such compounds.

In some embodiments of the invention, a weight ratio of the hydroxymethyl-substituted phosphorus compound(s) to tris(hydroxymethyl)nitromethane is from 7:1 to 1:12, alternatively from 8:1 to 1:9, alternatively from 7:1 to 1:9, alternatively from 7:1 to 1:8, alternatively from 6:1 to 1:12, alternatively from 6:1 to 1:10, alternatively from 6:1 to 1:9, alternatively from 6:1 to 1:8; alternatively from 5:1 to 1:12, alternatively from 5:1 to 1:10, alternatively from 5:1 to 1:9, alternatively from 5:1 to 1:8; alternatively from 4:1 to 1:12, alternatively from 4:1 to 1:10, alternatively from 4:1 to 1:9, alternatively from 4:1 to 1:8; alternatively from 3:1 to 1:12, alternatively from 3:1 to 1:9, alternatively from 3:1 to 1:10, alternatively from 3:1 to 1:8. In some embodiments of the invention, the composition is used to prevent microbial growth in a medium at higher temperatures and high sulfide levels, i.e., at least 50° C. and 2 ppm sulfide, conditions which typically are present in oil and gas wells and reservoirs. In these embodiments, the weight ratio of the hydroxymethyl-substituted phosphorus compound to tris(hydroxymethyl)nitromethane is from 1:1.5 to 1:12; alternatively from 1:1.5 to 1:10; alternatively from 1:1.5 to 1:9; alternatively from 1:1.5 to 1:8; alternatively from 1:1.8 to 1:12; alternatively from 1:1.8 to 1:10; alternatively from 1:1.8 to 1:9; alternatively from 1:1.8 to 1:8; alternatively from 1:2 to 1:12; alternatively from 1:2 to 1:10; alternatively from 1:2 to 1:9; alternatively from 1:2 to 1:8. In some embodiments of the invention, a higher temperature and high-sulfide medium is one having a temperature at least 60° C. and a sulfide level at least 4 ppm. In some embodiments, the temperature is at least 65° C.; alternatively at least 70° C.; alternatively at least 75° C.; alternatively at least 80° C. In some embodiments, the medium contains at least 5 ppm sulfide, alternatively at least 6 ppm sulfide, alternatively at least 7 ppm sulfide, alternatively at least 8 ppm sulfide, alternatively at least 9 ppm sulfide, alternatively at least 10 ppm sulfide. In some embodiments of the invention, the medium to which the antimicrobial composition is added is anaerobic. In some embodiments of the invention, the anaerobic medium is a high-temperature and high-sulfide environment. In some embodiments of the invention, the medium to which the antimicrobial composition is added contains sulfate-reducing bacteria. In some embodiments of the invention, the high-temperature and high-sulfide environment contains sulfate-reducing bacteria. In some embodiments of the invention, the medium to which the antimicrobial composition is added is an aqueous medium, i.e., one comprising at least 60% water, alternatively at least 80% water. In some embodiments of the invention, the aqueous medium is a high-temperature and high-sulfide medium.

In some embodiments of the invention, the antimicrobial combination of this invention is useful in oil and gas field injection, produced fluids, fracturing fluids and functional fluids, oil and gas wells, oil and gas operation, separation, storage, and transportation systems, oil and gas pipelines, oil and gas vessels, and fuel. The combination is especially useful in aqueous fluids added to or produced by oil and gas well. The composition also is useful for controlling microorganisms in other industrial water and water containing/contaminated matrixes, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, personal care and household products such as detergent, filtration systems (including reverse osmosis and ultrafiltration systems), toilet bowel, textiles, leather and leather production system, or a system used therewith.

Typically, the amount of the biocide combinations of the present invention to control the growth of microorganisms is from 10 ppm to 5,000 ppm active ingredient. In some embodiments of the invention, the active ingredients of the composition are present in an amount of at least 20 ppm, alternatively at least 50 ppm, alternatively at least 100 ppm, alternatively at least 150 ppm, alternatively at least 200 ppm. In some embodiments, the active ingredients of the composition are present in an amount of no more than 2,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are in a liquid composition containing the biocide combinations. Biocide concentrations in a high-sulfide and high-temperature environment typically will be higher than in other environments.

The present invention also encompasses a method for reducing, or inhibiting, or preventing microbial growth in the use areas described above, especially in oil or natural gas production operations, by incorporating the claimed biocide combination into the materials.

EXAMPLES

Example 1

Synergistic Effect of THPS and Tris Nitro Against Sulfate Reducing Bacteria (SRB)

Inside an anaerobic chamber (BACTRON anaerobic chamber), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic consortium, mainly SRB, at final bacterial concentrations of $10^6$ to $10^7$ CFU/mL. The aliquots of this contaminated water were then treated with THPS and Tris Nitro, or the THPS/Tris Nitro combination at different active concentration levels. After the mixtures were incubated at 40° C. for 24 hours, the biocidal efficacy was determined by minimum tested biocide concentration for bacteria kill in the aliquots (MBC). Table 1 summarizes the efficacy of each biocide and their blends, and the Synergy Index* of each combination.

TABLE 1

Biocidal efficacy of THPS, Tris Nitro, THPS/Tris Nitro combination, and Synergy Index

| Ratio of THPS to Tris Nitro (active w/w) | Average MBC (active ppm) THPS | Tris Nitro | Average Synergy Index[*1] | p value in ztest[*2] |
|---|---|---|---|---|
| 1:0 | 6.1 | 0.0 | | |
| 9:1 | 6.0 | 0.7 | 1.02 | 0.66 |
| 3:1 | 4.9 | 1.6 | 0.87 | 0.00 |
| 1:1 | 4.4 | 4.4 | 0.84 | 0.00 |
| 1:3 | 3.8 | 11.5 | 0.90 | 0.03 |
| 1:9 | 2.5 | 22.6 | 0.93 | 0.08 |
| 0:1 | 0.0 | 46.1 | | |

[*1]Synergy Index = Ca/CA + Cb/CB
Ca: Concentration of biocide A required to achieve a certain level of bacterial kill when used in combination
CA: Concentration of biocide A required to achieve a certain level of bacterial kill when used alone
Cb: Concentration of biocide B required to achieve a certain level of bacterial kill when used in combination
CB: Concentration of biocide B required to achieve a certain level of bacterial kill when used alone
[*2]p value < 0.05 means that there is significant difference between the average Synergy Index and 1.00

Example 2

Evaluation of Biocidal Efficacy of THPS, Tris Nitro, and Their Combination Against Anaerobic Bacteria for a High Temperature and Sulfide-Rich Environment Inside an anaerobic chamber (BACTRON IV), biocides solutions were challenged with $10^4$ to $10^5$ CFU/mL of an oilfield SRB consortium and 10 ppm sulfide ion (added in the form of sodium sulfide). The biocide solutions were then incubated at 80° C. under anaerobic condition for 7 days. Then the biocidal efficacy was evaluated against the field SRB consortium. The biocidal efficacy was determined by the biocide dosage required for 99.999% bacterial reduction. Synergy Index was then calculated. Table 2 summarizes the efficacy of each biocide and their blends, and the Synergy Index* of each combination.

TABLE 2

Biocidal efficacy evaluation of THPS, Tris Nitro, and THPS/Tris Nitro combination for a high temperature and sulfide-rich environment, and Synergy Index

| Ratio of THPS to Tris Nitro (active w/w) | Concentration (active ppm) required for 99.999% bacterial reduction (active ppm) THPS | Tris Nitro | Synergy Index |
|---|---|---|---|
| 1:0 | 360.0 | 0.0 | |
| 2:1 | >180 | >90 | >0.75 |
| 1:1 | >180 | >180 | >1 |
| 1:2 | 90 | 180 | 0.75 |
| 1:4 | 45 | 180 | 0.63 |
| 1:8 | 22.5 | 180 | 0.56 |
| 0:1 | 0 | 360 | |

Table 2 shows that the THPS and Tris Nitro combination was synergistic for a high temperature and sulfide-rich environment.

The invention claimed is:

1. A method for inhibiting microbial growth in a medium at a temperature of at least 60° C. and a sulfide level at least 4 ppm; said method comprising adding to the medium: (a) tetrakis(hydroxymethyl)phosphonium sulfate; and (b) tris(hydroxymethyl)nitromethane; wherein a weight ratio of tetrakis(hydroxymethyl)phosphonium sulfate to tris(hydroxymethyl)nitromethane is from 1:2 to 1:8.

2. The method of claim 1 in which the temperature is at least 70° C. and a sulfide level at least 7 ppm; and in which said weight ratio is from 1:2 to 1:8.

3. The method of claim 2 in which the medium is anaerobic and contains sulfate-reducing bacteria.

* * * * *